United States Patent
Yasuhara et al.

(10) Patent No.: US 6,660,803 B1
(45) Date of Patent: Dec. 9, 2003

(54) METHOD OF PREPARING (PERFLUOROALKYL) ETHYL ACRYLIC ESTERS AND METHODS OF PREPARING COPOLYMERS USING SAID ESTERS

(75) Inventors: Takashi Yasuhara, Osaka (JP); Shigeharu Iida, Osaka (JP); Osamu Yamamoto, Osaka (JP); Toshitaka Nakano, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/030,243

(22) PCT Filed: Jun. 27, 2000

(86) PCT No.: PCT/JP00/04201

§ 371 (c)(1),
(2), (4) Date: Jan. 9, 2002

(87) PCT Pub. No.: WO01/04081

PCT Pub. Date: Jan. 18, 2001

(30) Foreign Application Priority Data

Jul. 9, 1999 (JP) ............................................. 11-195967

(51) Int. Cl.⁷ ............................................... C08H 3/00
(52) U.S. Cl. ...................... 524/805; 524/832; 526/245; 526/250; 526/252
(58) Field of Search ................. 524/805, 832; 526/250, 245, 252

(56) References Cited

U.S. PATENT DOCUMENTS

| | | | | |
|---|---|---|---|---|
| 3,966,801 A | * | 6/1976 | Diamond .................... | 562/496 |
| 4,123,540 A | * | 10/1978 | Howarth ................ | 514/210.06 |
| 4,666,977 A | * | 5/1987 | Kihara et al. ............... | 524/805 |
| 4,859,793 A | | 8/1989 | Hurtel ........................ | 560/223 |
| 5,183,839 A | * | 2/1993 | Aharoni .................... | 524/113 |
| 5,283,045 A | | 2/1994 | Boenigk et al. ............ | 423/445 |
| 5,440,008 A | | 8/1995 | Ichikawa et al. ........... | 528/361 |
| 5,670,573 A | * | 9/1997 | Kirchner et al. ............... | 525/7 |
| 5,843,334 A | * | 12/1998 | Saheki et al. ................. | 516/51 |
| 6,284,853 B1 | * | 9/2001 | Yamana et al. ............. | 526/245 |

FOREIGN PATENT DOCUMENTS

| | | |
|---|---|---|
| EP | 206899 | 12/1986 |
| EP | 0 332 141 A2 | 9/1989 |
| EP | 0 414 155 A1 | 2/1991 |
| EP | 614874 | 9/1994 |
| EP | 0 710 685 A2 | 5/1996 |
| JP | 56-8457 A | 1/1981 |
| JP | 59-181239 | 10/1984 |
| JP | 7-2983 A | 1/1995 |
| JP | 7-53862 B2 | 6/1995 |
| JP | 7-173772 A | 7/1995 |
| JP | 7-78154 B2 | 8/1995 |
| JP | 8-9833 B2 | 1/1996 |
| JP | 9-31181 | 2/1997 |
| JP | 10-212325 | 8/1998 |

OTHER PUBLICATIONS

Buehler et al., Book: Survey of Organic Synthesis, (1970), see p. 817 and 825.*
March, J., Book: Advanced Organic Chemistry, 2nd Ed., (1977), see p. 367–368.*

* cited by examiner

Primary Examiner—David W. Wu
Assistant Examiner—Henry S Hu
(74) Attorney, Agent, or Firm—Birch, Stewart, Kolasch & Birch, LLP

(57) ABSTRACT

A polyfluoroalkyl iodide is reacted with a (meth)acrylic acid metal salt to form a corresponding polyfluoroalkyl (meth) acrylate ester. The polyfluoroalkyl (meth)acrylate ester is separated from the reaction product through the evaporation, so that the ester is recovered. According to the present method, the polyfluoroalkyl iodide is reacted with the (meth) acrylic acid metal salt without introducing water, thus making it possible to prepare a polyfluoroalkyl (meth)acrylate ester. The resulting ester can also be used to copolymerize an ethylenically unsaturated compound capable of copolymerizing with the ester.

20 Claims, 2 Drawing Sheets

[Fig. 1]
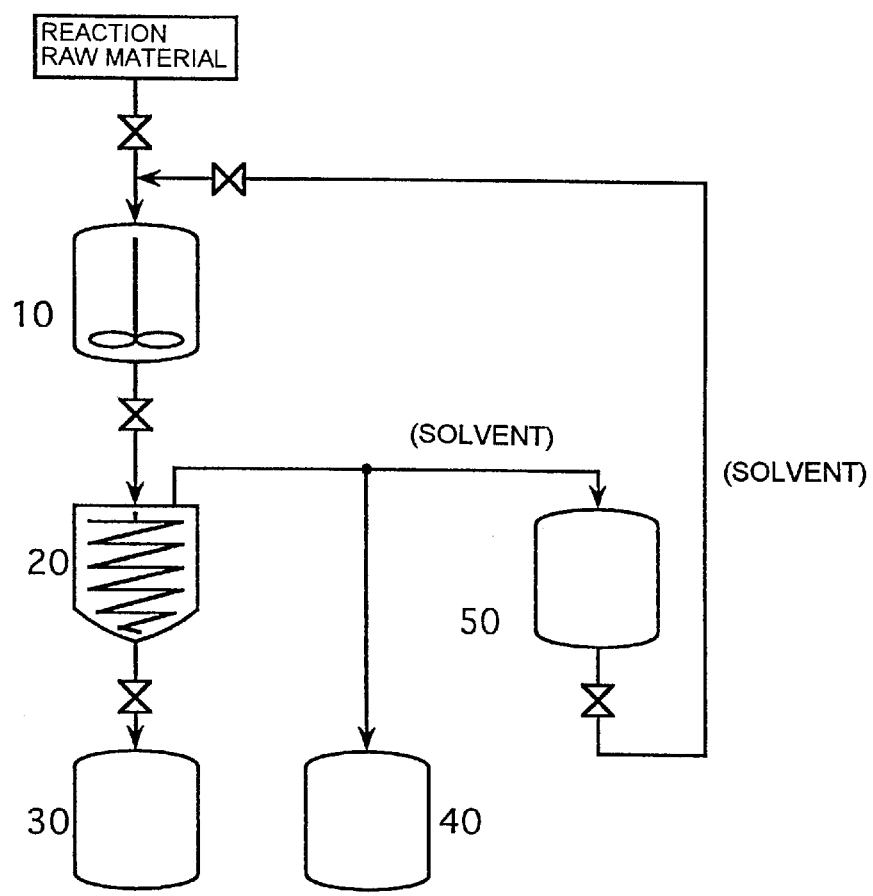

[Fig. 2]
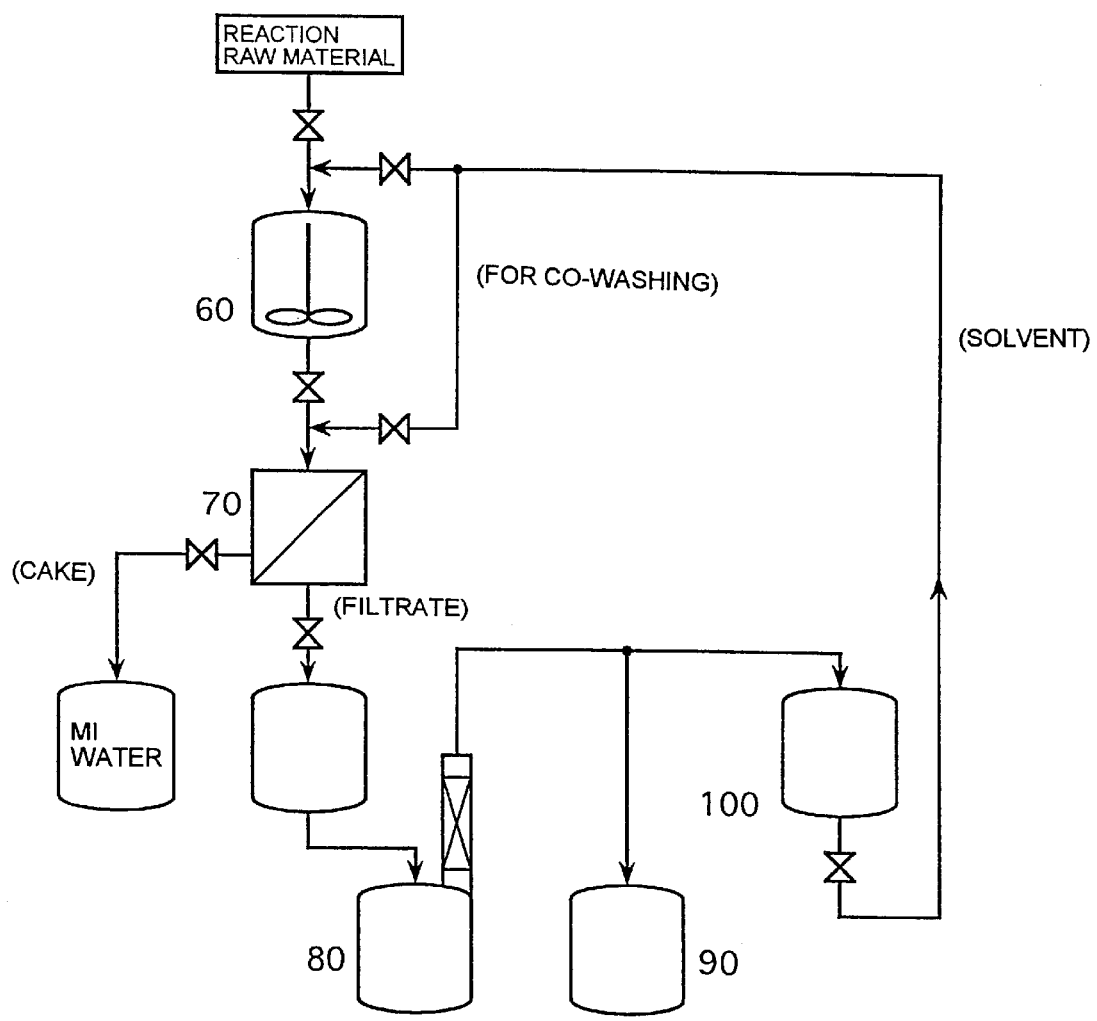

METHOD OF PREPARING (PERFLUOROALKYL) ETHYL ACRYLIC ESTERS AND METHODS OF PREPARING COPOLYMERS USING SAID ESTERS

This application is the national phase under 35 U.S.C. §371 of PCT International Application No. PCT/JP00/04201 which has an International filing date of Jun. 27, 2000, which designated the United States of America.

TECHNICAL FIELD

The present invention relates to a first method of preparing a polyfluoroalkyl (meth)acrylate ester, and a second method of preparing a fluorine-containing acrylic copolymer using the ester obtained by the first method.

RELATED ART

A (meth)acrylate ester having a perfluoroalkyl group and a fluorine-containing acrylic copolymer obtained through copolymerization of the (meth)acrylate ester and a monomer, which is capable of copolymerizing with the ester, have been used to impart water- and oil-repellency to textile products.

A polyfluoroalkyl (meth)acrylate ester to be used as a raw material in an industrial method of preparing such a fluorine-containing acrylic copolymer has conventionally been prepared by an operation as follows:

A polyfluoroalkyl iodide having a perfluoroalkyl group corresponding to the above ester is reacted with a (meth) acrylic acid metal salt (for example, potassium salt) in a proper solvent (for example, tert-butanol) (for example, in an ester-forming reaction apparatus 60 in FIG. 2) to obtain, as a reaction product, a suspension containing the polyfluoroalkyl (meth)acrylate ester and the metal iodide (for example, potassium iodide) precipitate derived from the (meth)acrylic acid metal salt. Then, the suspension is subjected to a filtration to separate the metal iodide (potassium iodide) as a solid material from a filtrate. The filtrate is thereafter subjected to a distillation to obtain the polyfluoroalkyl (meth)acrylate ester by separating the solvent (tert-butanol), which solvent may be then recycled.

According to the method described above, as shown in FIG. 2, in the step of filtering the metal iodide in a filtering apparatus 70, a product-based suspension is filtered and co-washed with a solvent, and thereby the polyfluoroalkyl (meth)acrylate ester in a filter cake is dissolved and recovered. Then, water is added to the filter cake and the metal iodide is discharged from the filtering apparatus in the form of an aqueous solution, while the filtering apparatus 70 is dried by heating for the following filtering step. The product-based filtrate separated previously is mixed with the solvent used for co-washing and the mixture is transferred to an evaporator 80, where the solvent and the polyfluoroalkyl (meth)acrylate ester are distilled off in order by a distillation operation, thereby to obtain a polyfluoroalkyl (meth)acrylate ester as a desired product, in an ester receiver 90 and to recover the solvent in a solvent tank 100.

DISCLOSURE OF INVENTION

According to the method including such a filtering step, since the metal iodide is discharged from the filtering apparatus 70 in a form of aqueous solution thereof by addition of water to the filter cake of the metal iodide, a small amount of water is introduced into the solvent in the following filtering step of the product-based suspension, resulting in incorporation of water along with the solvent into the reaction product. This water is easily miscible with the solvent such as tert-butanol and then accumulated in the solvent after being introduced into the solvent. In the case where a dehydration operation of the solvent is not carried out, water is circulated along with the solvent to the ester-forming reaction step.

However, since water inhibits the reaction of forming the polyfluoroalkyl (meth)acrylate ester from the polyfluoroalkyl iodide and the (meth)acrylic acid metal salt, the existence of water in the solvent is not preferable. Therefore, it was required to carry out a dehydration treatment if the water content in the solvent was increased before introducing the solvent into the ester-forming reaction step.

Accordingly, if the polyfluoroalkyl (meth)acrylate ester can be prepared without introducing water into the reaction system, the yield of the ester-forming reaction can be improved, and furthermore, the operation of dehydrating the solvent can be omitted, thus turning to its advantage in view of equipment cost.

An object of the present invention is to solve the problems described above and to provide a method of preparing a polyfluoroalkyl (meth)acrylate ester, which is to be used as a raw material of a fluorine-containing acrylic copolymer, without introducing water into the reaction system.

The present invention provides, in one aspect, a method of preparing a polyfluoroalkyl (meth)acrylate ester, which comprises the steps of:

(I) reacting a polyfluoroalkyl iodide with a (meth)acrylic acid metal salt to obtain a reaction mixture containing a polyfluoroalkyl (meth)acrylate ester and a metal iodide, as shown by the reaction scheme (Formula 1):

$$C_nF_{2n+1}CH_2CH_2I + CH_2=CXCOOM \rightarrow$$

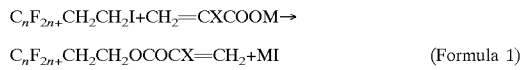

$$C_nF_{2n+1}CH_2CH_2OCOCX=CH_2 + MI \qquad \text{(Formula 1)}$$

[wherein X represents H or $CH_3$, n represents an integer within a range from 2 to 26, preferably from 8 to 20, and most preferably from 8 to 14, and M represents an alkali metal element]; and (II) heating the obtained reaction mixture to evaporate the polyfluoroalkyl (meth)acrylate ester, thereby to separate and recover the polyfluoroalkyl (meth)acrylate ester.

The present invention provides, in another aspect, a method of preparing a fluorine-containing acrylic copolymer, which comprises the step (step (III)) of copolymerizing the polyfluoroalkyl (meth)acrylate ester prepared by the method described above with an ethylenically unsaturated compound capable of copolymerizing with the above ester.

BRIEF DESCRIPTION OF DRAWINGS

FIG. 1 is a schematic illustration showing an embodiment of an apparatus which can be used to effect the method of preparing a polyfluoroalkyl (meth)acrylate ester of the present invention.

FIG. 2 is a schematic illustration showing an embodiment of an apparatus which can be used to effect the method of preparing a polyfluoroalkyl (meth)acrylate ester of the prior art.

BEST MODE FOR CARRYING OUT THE INVENTION

Describing with reference to the accompanying drawings, the step (I) of the method of preparing a fluorine-containing acrylic copolymer according to the present invention is carried out in an ester-forming reaction apparatus 10 shown in FIG. 1. In the ester-forming reaction apparatus 10, a polyfluoroalkyl iodide represented by the formula 2:

$$C_nF_{2n+1}CH_2CH_2I \quad \text{(Formula 2)}$$

[wherein n represents an integer within a range from 2 to 26, and preferably from 8 to 20] and a (meth)acrylic acid metal salt, as raw materials, are charged and then the ester-forming reaction is carried out to obtain a polyfluoroalkyl (meth)acrylate ester represented by the formula 3:

$$C_nF_{2n+1}CH_2CH_2OCOCX=CH_2 \quad \text{(Formula 3)}$$

[wherein X represents H or $CH_3$].

A polyfluoroalkyl group in the polyfluoroalkyl iodide used herein has a structure that an ethylene group ($CH_2CH_2$) is added to a polyfluoroalkyl group ($C_nF_{2n+1}$). Most preferably, n is an integer within a range from 8 to 14.

The (meth)acrylic acid metal salt may be a metal salt such as sodium, potassium or lithium salt, and preferably a potassium salt.

Examples of the solvent, which can be used in this reaction step include n-butanol, sec-butanol, tert-butanol, amyl alcohol, tert-amyl alcohol, methyl isobutyl ketone, isopropyl alcohol, methyl ethyl ketone, amyl acetate, and acetonitrile. Among these solvents, tert-butanol is particularly preferable.

This reaction step can be carried out at a temperature within a range from 150 to 220° C. for 60 to 300 minutes by controlling a molar ratio of raw materials [molar ratio of the (meth)acrylic acid metal salt to the polyfluoroalkyl iodide] within a range from 1.0 to 1.25, preferably from 1.0 to 1.05, and controlling the water content in the reaction system within a range from 0.01 to 1.0% by weight, preferably 0.1% by weight or less.

In the step (II) of the method according to the present invention, the reaction product system from the step (I) containing the solvent, the metal iodide (MI) and the polyfluoroalkyl (meth)acrylate ester as the desired product is transferred to an evaporator 20 as shown in FIG. 1, where the solvent and the polyfluoroalkyl (meth)acrylate ester are separated from the metal iodide (MI) by evaporating them, and then MI and a material having a boiling point higher than that of the desired product, which may exist in certain cases, are substantially recovered in a MI receiver 30 as a residue.

Since the reaction product system, which is subjected to this evaporation operation, contains the solvent at an earlier stage of the operation and is in a heated state, the (meth) acrylic polyfluoroalkyl ester is in a molten state or a solution state of being partially dissolved in the solvent and the metal iodide is in a state of being suspended in the solution. Therefore, the viscosity of the system is low.

However, as evaporation operation of the solvent and the (meth)acrylic polyfluoroalkyl ester proceeds, the solvent disappears from the product system earlier than the (meth) acrylic polyfluoroalkyl ester because the solvent generally has a boiling point lower than that of the (meth)acrylic polyfluoroalkyl ester. The (meth)acrylic polyfluoroalkyl ester having a small numerical value of n (Formula 3), namely, those having a lower boiling point are evaporated and the content of those esters in the product system is gradually reduced. Then, since it turns into a condition where the metal iodide is suspended in the (meth)acrylic polyfluoroalkyl ester having a large numerical value of n, namely, the (meth)acrylic polyfluoroalkyl ester having a higher boiling point and higher melting point, the viscosity of the system is gradually increased.

Since the solvent is evaporated earlier than the (meth) acrylic polyfluoroalkyl ester in the operation of recovering the solvent and the (meth)acrylic polyfluoroalkyl ester, the solvent is taken out first and then recovered in a solvent tank 50 after necessary cooling or condensing. The (meth)acrylic polyfluoroalkyl ester component, which is evaporated thereafter, is recovered in an ester receiver 40 after necessary cooling or condensing. Usually, the boiling point of the solvent is about 80° C. and that of the (meth)acrylic polyfluoroalkyl ester is about 190° C. so that the difference in boiling point between the solvent and the ester is large. Therefore, the solvent and the (meth)acrylic polyfluoroalkyl ester are recovered in order by so-called simple distillation to obtain MI as a bottom, thus making it possible to carry out the recovering operation. Alternatively, the operation of evaporating the solvent and the (meth)acrylic polyfluoroalkyl ester and recovering them may be carried out by recovering both the solvent and the (meth)acrylic polyfluoroalkyl ester together by evaporation, followed by separating and recovering the (meth)acrylic polyfluoroalkyl ester from the solvent by distillation.

In the method of the present invention, only the polyfluoroalkyl (meth)acrylate ester is evaporated from a mixture of the polyfluoroalkyl (meth)acrylate ester and the metal iodide as the solid component after the solvent was completely evaporated (or distilled off), so that the liquid component is separated from the solid component by evaporating the liquid component. Therefore, the expression "the polyfluoroalkyl (meth)acrylate ester is evaporated" is used in the present description and claims.

In the case when the polyfluoroalkyl group is $C_nF_{2n+1}CH_2CH_2OCOCH=CH_2$ (n=8 to 20) in the system in which tert-butanol as the solvent, the polyfluoroalkyl (meth) acrylate ester and potassium iodide as the metal iodide exist in a ratio (on a weight basis) of 30:55:15, the viscosity of the system is within a range from 0.5 to 20 cP (centipoise) at the temperature of 100° C. Then, in the system in which the polyfluoroalkyl (meth)acrylate ester and the metal iodide exist in a ratio (on a weight basis) of 5:95 after all of the solvent and almost all of the polyfluoroalkyl (meth)acrylate ester are evaporated from this system, the viscosity of the system becomes 500 cP or more at the temperature of 100° C.

Accordingly, the evaporating operation of the present invention requires to use an evaporator which has a outstanding stirring efficiency and a heat-transfer efficiency to an object to be evaporated. Although evaporation can be carried out under a normal atmospheric pressure, it is preferable to lower the evaporation temperature by evaporating under a reduced pressure in order to have a material having a higher boiling point be evaporated.

In the case where the polyfluoroalkyl group is $C_{12}F_{25}CH_2CH_2OCOCH=CH_2$, the boiling point of the polyfluoroalkyl (meth)acrylate ester is about 170° C. at about 25 mmHg, and therefore, an evaporator capable of reducing the pressure to 1 to 25 mmHg is preferably used in the evaporating operation of the present invention. To carry out the evaporating operation at further lower temperature, it is preferred to use an evaporator capable of reducing the pressure to 1 to 15 mmHg, and more preferably 1 to 10 mmHg.

Accordingly, it is important to use an apparatus having an excellent heat transfer efficiency and a stirring efficiency as the evaporator in the step (II) of the present invention. It is preferred to use an evaporator having a jacketed heating means, having a helical blade as the stirring blade and also having a reverse conical shape at the lower portion of the evaporator.

Examples of such an evaporator include Vertical Cone Reactor (manufactured by Mitsubishi Heavy Industries., Ltd), Advanced Ribbon Reactor (manufactured by Mitsubishi Heavy Industries., Ltd), and Super Blend (manufactured by Sumitomo Heavy Industries, Ltd.). Vertical Cone Reactor is equipped with a corn-shaped tank and a helical blade having a spirally-wound ribbon-shaped stirring blade.

In the case where the step (II) is carried out using Vertical Cone Reactor, the solvent is evaporated by heating to about 120 to 145° C. under a pressure such as about normal atmospheric pressure and $RfCH=CH_2$ is evaporated by reducing the pressure to about 300 to 500 mmHg while maintaining the temperature, and then the pressure is reduced to about 5 to 10 mmHg and the temperature is increased to about 170 to 200° C., thereby to evaporate the (meth)acrylic polyfluoroalkyl ester, thus making it possible to separate MI. For example, in case of $C_8F_{17}CH_2CH_2OCOCH=CH_2$, the temperature is increased to 135° C. under a pressure of 0.01 MPa (gauge pressure) to obtain a solvent, followed by recovering $RfCH=CH_2$ as a by-product at −400 mmHg (gauge pressure). And then, the pressure is reduced to about −755 mmHg and the temperature is increased to 190° C. to obtain an polyfluoroalkyl acrylate ester. Then, the contents of the evaporator are cooled to 50° C. or lower to recover MI.

The (meth)acrylic polyfluoroalkyl ester can be prepared in the manner described above. The recovered solvent can be recycled to the ester-forming reaction step without further treatment because it contains substantially no water.

In the step of the method of preparing a polymer according to the present invention, a fluorine-containing acrylic copolymer is prepared by copolymerizing the polyfluoroalkyl (meth)acrylate ester, which was obtained through the first method of preparing the polyfluoroalkyl (meth)acrylate ester, with an ethylenically unsaturated compound capable of copolymerizing with the above polyfluoroalkyl (meth) acrylate ester.

In the copolymerization reaction, a polyfluoroalkyl (meth) acrylate ester represented by the formula 3, n being within a range from 6 to 22 may be used.

Specific examples of the ethylenically unsaturated compound (monomer), which is copolymerized with the polyfluoroalkyl (meth)acrylate ester in the second a method of preparing the fluorine-containing acrylic copolymer, are compounds included in the following groups (a), (b) and (c). However, the ethylenically unsaturated compound is not limited to these examples, and may be basically an ethylenically unsaturated compound capable of copolymerizing with a (meth)acrylic acid.

Examples of the group (a) include ethylene, vinyl acetate, vinyl chloride, vinylidene halide, (meth)acrylic acid, (meth) acrylonitrile, styrene, α-methylstyrene, p-methylstyrene, (meth)acrylamide, N-methylol (meth)acrylamide, hydroxymethyl (meth)acrylate, hydroxyethyl (meth) acrylate, hydroxypropyl (meth)acrylate, 3-chloro-2-hydroxypropyl (meth)acrylate, polyethylene glycol (meth) acrylate, polypropylene glycol (meth)acrylate, methoxypolyethylene glycol (meth)acrylate, methoxypolypropylene glycol (meth)acrylate, N,N-dimethylaminoethyl (meth)acrylate, N,N-diethylaminoethyl (meth)acrylate, glycidyl (meth)acrylate, tetrahydrofurfuryl (meth)acrylate, benzyl (meth)acrylate, phenoxyethyl (meth) acrylate, dicyclopentenyl (meth)acrylate, hydroxypropyltrimethylammonium chloride methacrylate, ethyltrimethylammonium chloride methacrylate, vinyl alkyl ether, alkyl vinyl ether halide, butadiene, isoprene, chloroprene, and maleic anhydride.

Examples of the group (b) include acrylates represented by the general formula (Formula 4):

(Formula 4)

[wherein $A^1$ represents a hydrogen atom or a methyl group, and $A^2$ represents an alkyl group represented by $C_mH_{2m+1}$ (m represents an integer of 1 to 30)].

Examples of the group (c) include compound represented by the formula 5:

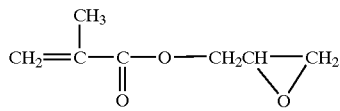

manufactured by KYOEISHA CHEMICAL Co., LTD. under the trade name of LIGHT-ESTER G), compound represented by the formula 6:

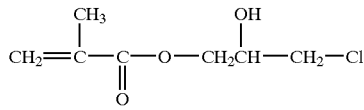

(manufactured by KYOEISHA CHEMICAL Co., LTD. under the trade name of LIGHT-ESTER CL), compound represented by the formula 7:

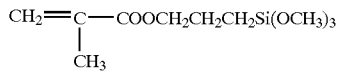

(manufactured by DOW CORNING TORAY SILICONE CO., LTD. under the trade name of SZ6030), compound represented by the formula 8:

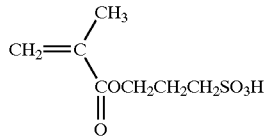

compound represented by the formula 9:

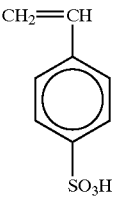

and compound (sulfonic acid-containing monomer) represented by the formula 10:

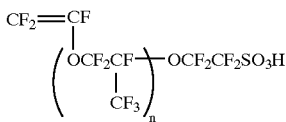

(n=1 to 20).

In the copolymerization according to the method of preparing the fluorine-containing acrylic copolymer, one or two or more kinds of the polyfluoroalkyl (meth)acrylate esters may be copolymerized with one or two or more kinds of the ethylenically unsaturated compounds.

The reaction or operation of the copolymerization to be carried out according to the method of preparing the fluorine-containing acrylic copolymer is basically a known reaction and is disclosed, for example, in Japanese Patent Kokai Publication No. 10-212325.

In the copolymerization reaction carried out according to the present method of preparing the fluorine-containing acrylic copolymer, bulk polymerization, solution polymerization, suspension polymerization and emulsion polymerization methods can be used. Among these methods, an emulsion polymerization method is particularly preferred because products are often used in the presence of a water medium.

The resulting copolymer may be used in water and oil repellents as well as textile processing agents because the copolymer has improved properties in various characteristics such as stain proof properties such as decontaminability, water and oil repellency, and dyeing resistance, antistatic property, antifungal property, abrasion resistance, cleaning resistance, feeling, and dispersion stability to medium such as water. Therefore, the kind and proportion of each of the polyfluoroalkyl (meth)acrylate ester and the ethylenically unsaturated compound to be used in the copolymerization can be selected according to the purposes.

The emulsion polymerization is carried out in an aqueous medium and water as the medium is used in the amount within a range from about 1 to 3 parts by weight, and preferably from about 1.5 to 2.5 parts by weight, based on 1 part by weight of the sum total of the monomer components used in the polymerization.

As an emulsifier used in emulsification, various known emulsifiers selected from anionic, cationic, nonionic and amphoteric emulsifiers can be used. The emulsifier is used in the amount within a range from about 0.02 to 0.15 parts by weight, and preferably from about 0.07 to 0.10 parts by weight, based on 1 part by weight of the sum total of the monomer components used in the polymerization.

As a polymerization initiator, there can be used those which are generally used. For example, various polymerization initiators such as azo-type or peroxide-type polymerization initiators can be used. The polymerization initiator is used in an amount within a range from about 0.001 to 0.05 parts by weight, and preferably from about 0.008 to 0.012 parts by weight, based on 1 part by weight of the sum total of the monomer components used in the polymerization.

The emulsifying operation before the copolymerization, which is carried out according to the method of preparing the fluorine-containing acrylic copolymer, is generally carried out at the temperature within a range from 40 to 80° C., and preferably from 50 to 60° C., in view of physical properties, especially melting point, of the polyfluoroalkyl acrylate ester and ethylenically unsaturated compound as raw materials of the copolymer. The solid content in the system to be emulsified is preferably within a range from 5 to 65%, and preferably from 20 to 40% (based on the total weight).

In the method of preparing the fluorine-containing acrylic copolymer, an emulsifying treatment of a solution to be treated, comprising a mixture of the polyfluoroalkyl (meth) acrylate ester and the ethylenically unsaturated compound, which are to be copolymerized, is carried out by using a high-pressure emulsifying apparatus to form emulsion particles having a particle size within a range from 0.001 to 1 $\mu$m, preferably from 0.01 to 0.5 $\mu$m, and most preferably from 0.01 to 0.2 $\mu$m. The reason why the particle size of the emulsion particles is controlled to about 1 $\mu$m or less before the copolymerization is as follows. That is, when emulsion particles having a particle size more than 1 $\mu$m exist in the system to be polymerized in the polymerization operation, coagulates are liable to be formed. By setting the maximum particle size of the emulsion particles to 1 $\mu$m or less, formation of coagulates may be prevented, thereby making it possible to carry out stable emulsion polymerization and to distribute the desired copolymer product within the particles of the emulsion polymer product almost uniformly.

To achieve such emulsification, a high-pressure emulsifying apparatus such as Gaulin Homogenizer (Manton Gaulin Laboratory Homogenizer 15M-6TA manufactured by Gaulin Inc.) or ultra-fine particles dispersion emulsifying apparatus) (Microfluidizer MIIO-E/H manufactured by Microfluidics Corp. or Mizuho-Kogyo, Co. Ltd.) can be used in combination with a conventional emulsifying apparatus, which employs a shear action, such as homomixer (T.K. Homomixer Mark II manufactured by Tokusyu Kika Kogyo Co., Ltd.) or ultramixer (vacuum stirring apparatus manufactured by Mizuho-Kogyo Co., Ltd.).

When using GAULIN HOMOGENIZER in the emulsification of the step (III) of the present invention, emulsification can be carried out by colliding a mixture to be emulsified against a metal plate at a pressure within a range from 150 to 700 kg/m$^2$, and generally 400 kg/m$^2$ on average. When using Microfluidizer, emulsification can be carried out at the pressure within a range from 200 to 2000 kg/m$^2$, and generally from 1500 to 2000 kg/m$^2$.

Microfluidizer generally used is that of a liquid-liquid collision type (Y type chamber) in comparison with GAULIN HOMOGENIZER, and the emulsion can be controlled by using in combination with a Z type one for back pressure. This apparatus is a high-pressure emulsifying apparatus having such advantages that the mechanical noise thereof is small and a constant pressure is available since it employs a hydraulic pressure to secure a high pressure.

When a common solution is applied to the emulsification using a conventional dispersion mixer such as homomixer or ultramixer and a high-pressure emulsifying machine, respectively, emulsion particles having an particle size within a range from about 0.7 $\mu$m to 1.0 mm are obtained and it is scarcely expected that the upper limit value of the emulsion particles is controlled to 1 $\mu$m in the former case. On the other hand, in the latter case using the high-pressure emulsifying machine, emulsion particles having an particle size within a range from about 0.01 to 0.5 $\mu$m are obtained, thus making it possible to control the upper limit value of the emulsion particles to 1 $\mu$m.

Therefore, the high-pressure emulsifying machine is preferably used in the emulsifying treatment which is carried out in the method of preparing the fluorine-containing acrylic copolymer of the present invention. In the case where the solution to be treated, which is to be emulsified, exists in a large amount, even if the solution to be treated in a condition of forming a mixture to be emulsified is directly introduced into the high-pressure emulsifying machine, it takes a long time to obtain emulsion particles having a desired uniform particle size, for example, a particle size within a range from about 0.01 to 0.5 µm, resulting in poor efficiency. Therefore, a conventional dispersion mixer (homomixer or ultramixer) can be used in combination with the high-pressure emulsifying apparatus. In such a case, a conventional emulsifying apparatus can also be used in pre-treatment of high-pressure emulsification. Alternatively, a conventional emulsifying apparatus can be connected in series or in parallel with the high-pressure emulsifying apparatus through arranging conduits.

INDUSTRIAL APPLICABILITY

According to the method of preparing a polyfluoroalkyl (meth)acrylate ester of the present invention, the yield of the ester-forming reaction was enhanced from 80% to 88% by preventing water from introducing into the reaction system. The recovered solvent (tert-butanol) could be recycled to the ester-forming reaction step without further treatment because it was free from water.

Accordingly, it has been found that the constitution of the method of preparing a polyfluoroalkyl (meth)acrylate ester of the present invention can be made simple as compared with a conventional preparation method, and furthermore, the polyfluoroalkyl (meth)acrylate ester can be prepared advantageously as compared with the prior art, with respect to the yield and equipment cost.

As described above, the quality of the copolymer obtained by the method of preparing a fluorine-containing acrylic copolymer of the present invention is improved by employing high-pressure emulsification.

EXAMPLES

Example 1

Step (I):

Using, as a reaction apparatus, a pressure-resistant (proof pressure: 30 kg/cm$^2$) SUS autoclave (volume: 1 liter) equipped with a high-efficiency stirring blade "FULLZONE" (manufactured by Shinko Pantec Company Ltd.), $C_8F_{17}CH_2CH_2I$ (500 g), potassium acrylate (93 g) and tert-butanol (350 g) were charged in this reaction apparatus and the ester-forming reaction was carried out.

In the ester-forming reaction step, the ester-forming reaction was carried under the conditions of a temperature of 175 to 185° C. for 3.0 to 4.0 hours. The analysis results of the product in the ester-forming reaction are as follows. An analysis by means of gas chromatography (GC) using a column SE-30 (3 m) revealed that (1) a conversion ratio of $C_8F_{17}CH_2CH_2I$ is 99.8%; and (2) a yield of $C_8F_{17}CH_2CH_2OCOCH=CH_2$ is 88%, a yield of $C_8F_{17}CH=CH_2$ is 10%, and a yield of $C_8F_{17}CH_2CH_2OH$ is 1% or less. As a result of the measurement by means of gas chromatography, the yield of a polyfluoroalkyl acrylate ester was 88%.

Step (II):

The reaction product (943 g) from the above step (I) was transferred to Vertical Cone Reactor having a volume of 1 liter and heated to 135° C. under normal pressure, thereby to recover 340 g of tert-butanol. Then, the pressure was reduced to 360 mmHg (gauge pressure: −400 mmHg) while maintaining the temperature to recover $RfCH=CH_2$ as by-products. Then, after reducing the pressure to about 5 mmHg, stirring was carried out while raising the temperature to about 190° C. by jacket heating, thereby to evaporate the liquid component.

The gas component discharge portion of Vertical Cone Reactor may be provided with a condenser. In case Vertical Cone Reactor is provided with the condenser, tert-butanol used as the solvent and a polyfluoroalkyl acrylate ester as the desired product were recovered in order.

Example 2

Step (III):

360 g (0.69 mol) of the ester ($C_8F_{17}CH_2CH_2OCOCH=CH_2$) obtained in the above step (II) as the product thereof, 180 g (0.55 mol) of stearyl acrylate, 5.2 g of 3-chloro-2-hydroxypropyl methacrylate, 10.7 g of N-methylolacrylamide, 95 g of an emulsifier, 750 g of water and 110 g of dipropylene glycol monomethyl ether were charged in an autoclave of glass (separate type glass apparatus) having a volume of 2 liter and then preliminary emulsification was carried out at the temperature of 50 to 55° C. for 30 minutes using an ultramixer. The particle size of emulsion particles was measured by a particle size distribution measuring apparatus SALD-2100 (manufactured by Shimadzu Corporation). As a result, it was within a range from 0.6 to 1.0 µm.

While maintaining the temperature of the preliminary emulsion at 45 to 55° C., the preliminary emulsion was charged in a hopper of GAULIN HOMOGENIZER (SUS, 1 liter) and high-pressure emulsification was carried out. Although the emulsifying method includes a cycle emulsifying (circulating type) method and a pass emulsifying (passing type) method, the pass emulsifying method which is a more efficient method was employed in this Example. The emulsifying pressure was controlled to 450 kg/cm$^2$. With respect to the emulsifying temperature, the emulsifying machine outlet port temperature is preferably maintained at 55±5° C.

The particle size of emulsion particles was measured by a particle size distribution measuring apparatus SALD-2100 (manufactured by Shimadzu Corporation). As a result, it was within a range from 0.03 to 0.20 µm.

The high-pressure emulsified product thus obtained was transferred to a four-necked flask having a volume of 1 liter and, after controlling the liquid temperature to a temperature within a range from 50 to 60° C., dissolved oxygen was removed by replacement with nitrogen. Then, an azo-type polymerization initiator (V-50, manufactured by Wako Pure Chemicals Industries, Ltd.) was added and the copolymerization reaction was carried out at 60° C. for one hour.

The particle size of the resulting polymer composition was measured by a particle size distribution measuring apparatus SALD-2100 (manufactured by Shimadzu Corporation). As a result, the resulting polymer composition had an average particle size of 0.08 µm. As a result of a centrifugal sedimentation test (carried out under the conditions of a diameter of 10 cm at 5000 rpm for 30 minutes), no sediment was recognized.

Comparative Example 1

Using a conventional reaction apparatus shown in FIG. 2, a test for comparison with the present invention was carried out.

Using, as an ester-forming reaction apparatus, an autoclave of SUS having a volume of 1 liter, $C_8F_{17}CH_2CH_2I$ (500 g), potassium acrylate (93 g) and tert-butanol (350 g) were charged in this reaction apparatus and the ester-forming reaction was carried out. The conditions of the ester-forming reaction step were the same as those in

Example 1

To simulate the method of the prior art, tert-butanol having the water content of 2% by weight was used as tert-butanol in this Comparative Example 1.

The analysis results of the product in the ester-forming reaction are as follows.

An analysis revealed that (1) a conversion ratio of $C_8F_{17}CH_2CH_2I$ is 99.8%; and (2) a yield of $C_8F_{17}CH_2CH_2OCOCH=CH_2$ is 80%, a yield of $C_8F_{17}CH=CH_2$ is 10% and a yield of $C_8F_{17}CH_2CH_2OH$ is 6%.

943 g of the reaction product was collected by filtering through a 300 mesh wedge filter. As a result of the measurement by means of gas chromatography, the yield of a polyfluoroalkyl acrylate ester was 80%.

Comparative Example 2

Those having the same charge composition as in Example 2 were transferred to a four-necked flask having a volume of 1 liter after preliminary emulsification by a homomixer without carrying out high-pressure emulsification by GAULIN HOMOGENIZER. After controlling the liquid temperature to a temperature within a range from 50 to 60° C., dissolved oxygen was removed by replacement with nitrogen. Then, an azo-type polymerization initiator (V-50, manufactured by Wako Pure Chemicals Industries, Ltd.) was added and the copolymerization reaction was carried out at 60° C. for one hour.

The particle size of the resulting polymer composition was measured by a particle size distribution measuring apparatus SALD-2100 (manufactured by Shimadzu Corporation). As a result, the resulting polymer composition contained a polymer having a coarse particle size within a range from 1 to several tens u m and also contained 65 g of coagulates having a particle size within a range from 0.1 mm to several tens of mm in a wet state.

As compared with Example 2, the yield loss is about 15%. Since the polymer having a coarse particle size within a range from 1 μm to several tens of μm is liable to coagulate with a lapse of time to form particles having a more large particle size, which are liable to form sediments or suspended materials, thus making it possible to cause worsening of the quality.

What is claimed is:

1. A method of preparing a (perfluoroalkyl)ethyl (meth) acrylate ester, which comprises the steps of:
   (I) reacting a (perfluoroalkyl)ethyl iodide with a (meth) acrylic acid metal salt using a solvent having a boiling point lower than that of the aimed product to obtain a reaction mixture containing a (perfluoroalkyl)ethyl (meth)acrylate ester and a metal iodide, as shown by the reaction scheme (Formula 1):

$C_nF_{2n+1}CH_2CH_2I+CH_2=CXCOOM\rightarrow$ $C_nF_{2n+i}CH_2CH_2OCOCX=CH_2+MI$ (Formula 1)

wherein X represents H or $CH_3$, n represents an integer within a range from 2 to 26, and M represents an alkali metal element; and
   (II) heating the obtained reaction mixture in the absence of water in order to evaporate and separately recover the (perfluoroalkyl)ethyl (meth)acrylate from the metal iodide.

2. The method according to claim 1, wherein a polyfluoroalkyl iodide of the formula $C_nF_{2n+1}CH_2CH_2I$ is used in the step (I), n being an integer within a range from 8 to 20.

3. The method according to claim 1, wherein a salt of sodium or potassium is used as the (meth)acrylic acid metal salt in the step (I).

4. A method of preparing a fluorine-containing acrylic copolymer, which comprises the steps of:
   copolymerizing the (perfluoroalkyl)ethyl (meth)acrylate ester prepared through the method of claim 1, with an ethylenically unsaturated compound capable of copolymerizing with the ester.

5. A method of preparing a fluorine-containing acrylic copolymer, which comprises the steps of:
   copolymerizing the (perfluoroalkyl)ethyl (meth)acrylate ester prepared through the method of claim 2, with an ethylenically unsaturated compound capable of copolymerizing with the ester.

6. A method of preparing a fluorine-containing acrylic copolymer, which comprises the steps of:
   copolymerizing the (perfluoroalkyl)ethyl (meth)acrylate ester prepared through the method of claim 3, with an ethylenically unsaturated compound capable of copolymerizing with the ester.

7. The method according to claim 4, which comprises emulsifying a solution comprising a mixture of the (perfluoroalkyl)ethyl (meth)acrylate ester and the ethylenically unsaturated compound, which are to be copolymerized, in a predetermined medium using a high-pressure emulsifying means to form emulsion particles having a particle size within a range from 0.001 to 1 μm; and copolymerizing the emulsion particles by emulsion polymerization.

8. The method according to claim 5, which comprises emulsifying a solution comprising a mixture of the (perfluoroalkyl)ethyl (meth)acrylate ester and the ethylenically unsaturated compound, which are to be copolymerized, in a predetermined medium using a high-pressure emulsifying means to form emulsion particles having a particle size within a range from 0.001 to 1 μm; and copolymerizing the emulsion particles by emulsion polymerization.

9. The method according to claim 6, which comprises emulsifying a solution comprising a mixture of the (perfluoroalkyl)ethyl (meth)acrylate ester and the ethylenically unsaturated compound, which are to be copolymerized, in a predetermined medium using a high-pressure emulsifying means to form emulsion particles having a particle size within a range from 0.001 to 1 μm; and copolymerizing the emulsion particles by emulsion polymerization.

10. The method according to claim 7, wherein a microfluidizer is used as the high-pressure emulsifying means.

11. The method according to claim 8, wherein a microfluidizer is used as the high-pressure emulsifying means.

12. The method according to claim 9, wherein a microfluidizer is used as the high-pressure emulsifying means.

13. The method according to claim 4, wherein at least one compound selected from acrylates represented by the general formula (Formula 4):

$CH_2=CA^1COOA^2$ (Formula 4)

wherein $A^1$ represents a hydrogen atom or a methyl group, $A^2$ represents an alkyl group represented by $C_mH_{2m+1}$, and m represents an integer of 1 to 30, is used as the ethylenically unsaturated compound.

14. The method according to claim 6, wherein at least one compound selected from acrylates represented by the general formula (Formula 4):

$CH_2=CA^1COOA^2$ (Formula 4)

wherein $A^1$ represents a hydrogen atom or a methyl group, $A^2$ represents an alkyl group represented by $C_mH_{2m+1}$, and m represents an integer of 1 to 30, is used as the ethylenically unsaturated compound.

15. The method according to claim 8, wherein at least one compound selected from acrylates represented by the general formula (Formula 4):

$$CH_2=CA^1COOA^2 \qquad \text{(Formula 4)}$$

wherein $A^1$ represents a hydrogen atom or a methyl group, $A^2$ represents an alkyl group represented by $C_mH_{2m+1}$, and m represents an integer of 1 to 30, is used as the ethylenically unsaturated compound.

16. The method according to claim 9, wherein at least one compound selected from acrylates represented by the general formula (Formula 4):

$$CH_2=CA^1COOA^2 \qquad \text{(Formula 4)}$$

wherein $A^1$ represents a hydrogen atom or a methyl group, $A^2$ represents an alkyl group represented by $C_mH_{2m+1}$, and m represents an integer of 1 to 30, is used as the ethylenically unsaturated compound.

17. The method according to claim 10, wherein at least one compound selected from acrylates represented by the general formula (Formula 4):

$$CH_2=CA^1COOA^2 \qquad \text{(Formula 4)}$$

wherein $A^1$ represents a hydrogen atom or a methyl group, $A^2$ represents an alkyl group represented by $C_mH_{2m+1}$, and m represents an integer of 1 to 30, is used as the ethylenically unsaturated compound.

18. The method according to claim 11, wherein at least one compound selected from acrylates represented by the general formula (Formula 4):

$$CH_2=CA^1COOA^2 \qquad \text{(Formula 4)}$$

wherein $A^1$ represents a hydrogen atom or a methyl group, $A^2$ represents an alkyl group represented by $C_mH_{2m+1}$, and m represents an integer of 1 to 30, is used as the ethylenically unsaturated compound.

19. The method according to claim 1, wherein step (II) is conducted by heating the obtained reaction mixture using a stirring tank type evaporator having a jacketed heating means, having a helical blade as a stirring blade for high-viscosity material and also having a reverse conical shape at the lower portion of the evaporator to evaporate the (perfluoroalkyl)ethyl (meth)acrylate ester, thereby separating from each other and recovering the (perfluoroalkyl)ethyl (meth)acrylate ester and the metal iodide.

20. The method according to claim 1, wherein the water content in the reaction system is less than 1.0% by weight.

* * * * *